(12) United States Patent
Aoki et al.

(10) Patent No.: US 10,408,149 B2
(45) Date of Patent: Sep. 10, 2019

(54) CONTROL DEVICE FOR INTERNAL COMBUSTION ENGINE

(71) Applicants: Keiichiro Aoki, Shizuoka-ken (JP); Go Hayashita, Ebina (JP)

(72) Inventors: Keiichiro Aoki, Shizuoka-ken (JP); Go Hayashita, Ebina (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 181 days.

(21) Appl. No.: 14/441,681

(22) PCT Filed: May 24, 2013

(86) PCT No.: PCT/JP2013/064524
§ 371 (c)(1),
(2) Date: May 8, 2015

(87) PCT Pub. No.: WO2014/125661
PCT Pub. Date: Aug. 21, 2014

(65) Prior Publication Data
US 2015/0337752 A1  Nov. 26, 2015

(30) Foreign Application Priority Data
Feb. 18, 2013 (JP) .................. 2013-029168

(51) Int. Cl.
*F02D 41/14* (2006.01)
*G01N 27/406* (2006.01)
*G01N 27/407* (2006.01)

(52) U.S. Cl.
CPC ..... *F02D 41/1454* (2013.01); *F02D 41/1456* (2013.01); *G01N 27/4065* (2013.01); *G01N 27/4072* (2013.01)

(58) Field of Classification Search
CPC ............. G01N 27/407; G01N 27/4076; G01N 27/409; G01N 27/419; F02D 41/1454; F02D 41/1456
(Continued)

(56) References Cited

U.S. PATENT DOCUMENTS 4,140,085 A * 2/1979 Rabus ................. F02D 41/1496
123/693
4,153,023 A * 5/1979 Asano ................. F02D 41/1455
123/688
(Continued)

FOREIGN PATENT DOCUMENTS

CN  101091112 A  12/2007
DE  19652059 A1  6/1997
(Continued)

*Primary Examiner* — Jacob M Amick
*Assistant Examiner* — Michael A Kessler
(74) *Attorney, Agent, or Firm* — Hunton Andrews Kurth LLP (57) ABSTRACT

A sensor for detecting oxygen concentration in exhaust gas or an air-fuel ratio provided with a solid electrolyte body, an exhaust gas side electrode being disposed on one side of the solid electrolyte body and being in contact with the exhaust gas, an atmosphere side electrode being disposed on the other side of the solid electrolyte body and being in contact with the atmosphere, and an electric circuit applying a reference voltage between these electrodes is arranged in an engine exhaust passage. The sensor for detecting the oxygen concentration in the exhaust gas or the air-fuel ratio has a characteristic in which an output current continues to increase without having a limiting current region when the voltage applied between the electrodes is increased while the air-fuel ratio is constant. The air-fuel ratio is controlled based on the output current of the sensor for detecting the oxygen concentration in the exhaust gas or the air-fuel ratio.

5 Claims, 9 Drawing Sheets (58) Field of Classification Search
USPC .......... 123/672, 683; 73/114.71–114.73; 709/109; 205/783.5–784.5; 60/276
See application file for complete search history.

(56) References Cited

U.S. PATENT DOCUMENTS

| | | | | |
|---|---|---|---|---|
| 4,212,066 | A * | 7/1980 | Carp | F02D 41/06 123/486 |
| 4,366,039 | A * | 12/1982 | Uchida | G01N 27/4071 204/406 |
| 4,566,419 | A * | 1/1986 | Ninomiya | F02D 41/1476 123/681 |
| 5,338,431 | A * | 8/1994 | Yorita | G01N 27/4065 123/704 |
| 5,405,521 | A * | 4/1995 | Nakamori | F02D 41/1455 204/406 |
| 5,671,721 | A * | 9/1997 | Aoki | F02D 41/1494 123/688 |
| 5,709,198 | A * | 1/1998 | Sagisaka | F02D 41/1455 123/684 |
| 5,777,204 | A | 7/1998 | Abe | |
| 5,833,836 | A | 11/1998 | Takami et al. | |
| 6,055,972 | A | 5/2000 | Fujimoto et al. | |
| 6,214,209 | B1 * | 4/2001 | Gruenwald | G01N 27/4071 204/425 |
| 6,382,015 | B1 | 5/2002 | Aoki | |
| 6,440,283 | B1 | 8/2002 | Liu | |
| 2006/0047468 | A1 | 3/2006 | Aoki | |
| 2007/0261960 | A1 | 11/2007 | Aoki | |

FOREIGN PATENT DOCUMENTS

| | | |
|---|---|---|
| EP | 2952717 A1 | 9/2015 |
| JP | 62145161 A | 6/1987 |
| JP | 04-013961 A | 1/1992 |
| JP | 10-082760 A | 3/1998 |
| JP | 2000-065784 A | 3/2000 |
| JP | 2000-111512 A | 4/2000 |
| JP | 2002-022699 A | 1/2002 |
| JP | 2006-291893 A | 10/2006 |
| JP | 2008-008668 A | 1/2008 |
| JP | 2008-095663 A | 4/2008 |
| JP | 2009-121401 A | 6/2009 |
| WO | 2005/022141 A1 | 3/2005 |

* cited by examiner

CONTROL DEVICE FOR INTERNAL COMBUSTION ENGINE

CROSS-REFERENCE TO RELATED APPLICATIONS

This is a national phase application based on the PCT International Patent Application No. PCT/JP2013/064524 filed May 24, 2013, claiming priority to Japanese Patent Application No. 2013-029168 filed Feb. 18, 2013, the entire contents of both of which are incorporated herein by reference.

TECHNICAL FIELD

The invention relates to a control device for an internal combustion engine.

BACKGROUND ART

A control device for an internal combustion engine in which an oxygen concentration sensor that is provided with a solid electrolyte body, an exhaust gas side electrode being disposed on one side of the solid electrolyte body and being in contact with the exhaust gas, a reference gas side electrode being disposed on the other side of the solid electrolyte body and being in contact with reference gas, and a diffusion velocity layer covering the exhaust gas side electrode is arranged in an engine exhaust passage and an air-fuel ratio is controlled based on an output of the oxygen concentration sensor is known (refer to Patent Literature 1). This oxygen concentration sensor generates an output voltage higher than a reference voltage corresponding to a theoretical air-fuel ratio when the air-fuel ratio is lower than the theoretical air-fuel ratio and generates an output voltage lower than the reference voltage when the air-fuel ratio is higher than the theoretical air-fuel ratio. Accordingly, it is determined that the air-fuel ratio is lower than the theoretical air-fuel ratio and the air-fuel ratio is controlled to be increased when the output voltage is higher than the reference voltage. It is determined that the air-fuel ratio is higher than the theoretical air-fuel ratio and the air-fuel ratio is controlled to be decreased when the output voltage is lower than the reference voltage. In this case, the diffusion velocity layer has the function of controlling the diffusion rate of the exhaust gas. In this oxygen concentration sensor, no voltage is applied between the exhaust gas side electrode and the reference gas side electrode.

CITATION LIST

Patent Literature

Patent Literature 1: Japanese Patent Application Publication No. 2006-291893

SUMMARY OF THE INVENTION

Technical Problem

In Patent Literature 1, however, the exhaust gas side electrode is covered by a diffusion rate controlling layer, and thus the responsiveness of the oxygen concentration sensor is reduced. As a result, the output voltage of the oxygen concentration sensor is hysteretic. In other words, the output voltage change in a case where the air-fuel ratio increases across the theoretical air-fuel ratio and the output voltage change in a case where the air-fuel ratio decreases across the theoretical air-fuel ratio differ from each other. Accordingly, the output voltage may be lower than the reference voltage as the case may be, especially when the air-fuel ratio is close to the theoretical air-fuel ratio, regardless of the air-fuel ratio being lower than the theoretical air-fuel ratio and the output voltage may be higher than the reference voltage as the case may be regardless of the air-fuel ratio being higher than the theoretical air-fuel ratio. As a result, the air-fuel ratio cannot be accurately detected, and thus the air-fuel ratio may not be accurately controlled. Complex configurations and controls are required in order to address the problem.

Solution To Problem

The invention provides a control device for an internal combustion engine, in which a sensor for detecting oxygen concentration in exhaust gas or an air-fuel ratio provided with a solid electrolyte body, an exhaust gas side electrode being disposed on one side of the solid electrolyte body and being in contact with the exhaust gas, a reference gas side electrode being disposed on the other side of the solid electrolyte body and being in contact with reference gas, and an electric circuit applying a reference voltage between these electrodes is arranged in an engine exhaust passage, the sensor for detecting the oxygen concentration in the exhaust gas or the air-fuel ratio has a characteristic in which an output current continues to increase without having a limiting current region when the voltage applied between the electrodes is increased while the air-fuel ratio is constant, and the air-fuel ratio is controlled based on the output current of the sensor for detecting the oxygen concentration in the exhaust gas or the air-fuel ratio.

Effects Of The Invention

The air-fuel ratio can be accurately controlled by using a simple configuration.

MODES FOR CARRYING OUT THE INVENTION

Figure 1:
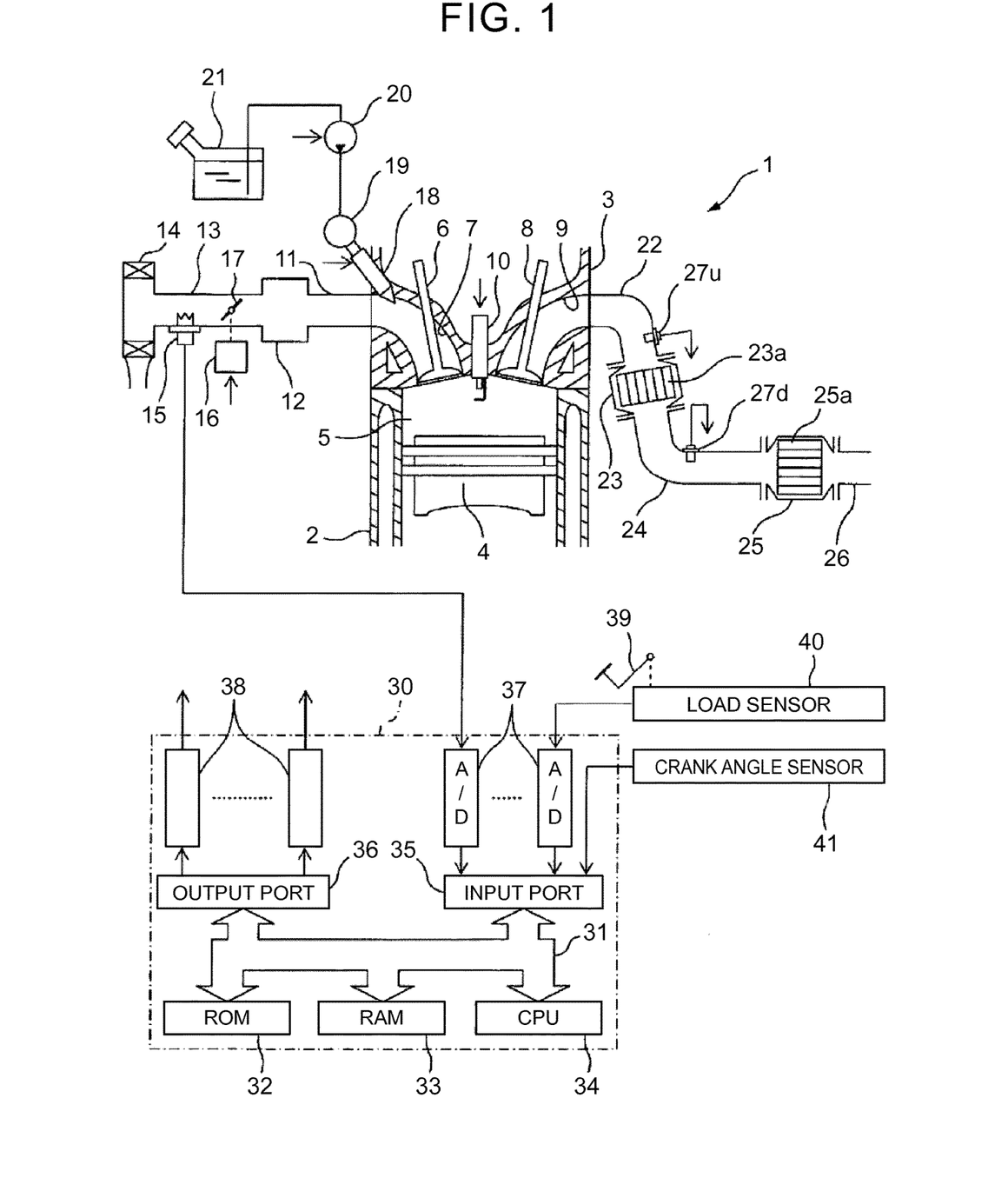
FIG. 1 is an overall view of an internal combustion engine.

FIG. 1 illustrates a case where the invention is applied to a spark-ignited internal combustion engine. However, the invention can also be applied to a compression-ignited internal combustion engine.

Referring to FIG. 1, 1 represents an engine main body that is provided with, for example, four cylinders, 2 represents a cylinder block, 3 represents a cylinder head, 4 represents a piston, 5 represents a combustion chamber, 6 represents an intake valve, 7 represents an intake port, 8 represents an exhaust valve, 9 represents an exhaust port, and 10 represents a spark plug. The intake port 7 is connected to a surge tank 12 via a corresponding intake branch pipe 11. The surge tank 12 is connected to an air cleaner 14 via an intake duct 13. An air flow meter 15 for intake air amount detection and a throttle valve 17 that is driven by an actuator 16 are arranged in the intake duct 13. An electronically-controlled fuel injection valve 18 is arranged in each of the intake ports 7. The fuel injection valves 18 are connected to a fuel pump 20 via a common rail 19 that is common to the fuel injection valves 18. The fuel pump 20 is connected to a fuel tank 21.

The exhaust port 9 is connected to a catalytic converter 23 that has a relatively small capacity via an exhaust manifold 22. The catalytic converter 23 is connected to a catalytic converter 25 that has a relatively large capacity via an exhaust pipe 24. The catalytic converter 25 is connected to an exhaust pipe 26. The catalytic converters 23, 25 are provided with catalysts, such as three-way catalysts 23a, 25a, therein, respectively. A sensor 27u for detecting oxygen concentration in exhaust gas or an air-fuel ratio is mounted on the exhaust manifold 22 on an upstream side of the three-way catalyst 23a. A sensor 27d for detecting oxygen concentration in exhaust gas or an air-fuel ratio is mounted on the exhaust pipe 24 on a downstream side of the three-way catalyst 23a. Hereinafter, the sensor 27u will be referred to as an upstream side sensor and the sensor 27d will be referred to as a downstream side sensor.

A digital computer constitutes an electronic control unit 30. The electronic control unit 30 is provided with a read-only memory (ROM) 32, a random access memory (RAM) 33, a microprocessor (CPU) 34, an input port 35, and an output port 36 connected to each other by a bidirectional bus 31. A load sensor 40 for detecting the amount of depression of an accelerator pedal 39 is mounted on the accelerator pedal 39. Output signals from the air flow meter 15, the sensor 27u, the sensor 27d, and the load sensor 40 are input to the input port 35 via AD converters 37 corresponding respectively thereto. In addition, a crank angle sensor 41, which generates an output pulse every time a crankshaft rotates at a predetermined angle, for example, 30 crank angle, is connected to the input port 35. The CPU 34 calculates an engine speed based on the output pulse from the crank angle sensor 41. The output port 36 is connected to each of the spark plug 10, the actuator 16, the fuel injection valve 18, and the fuel pump 20 via a corresponding drive circuit 38.

Figure 2:
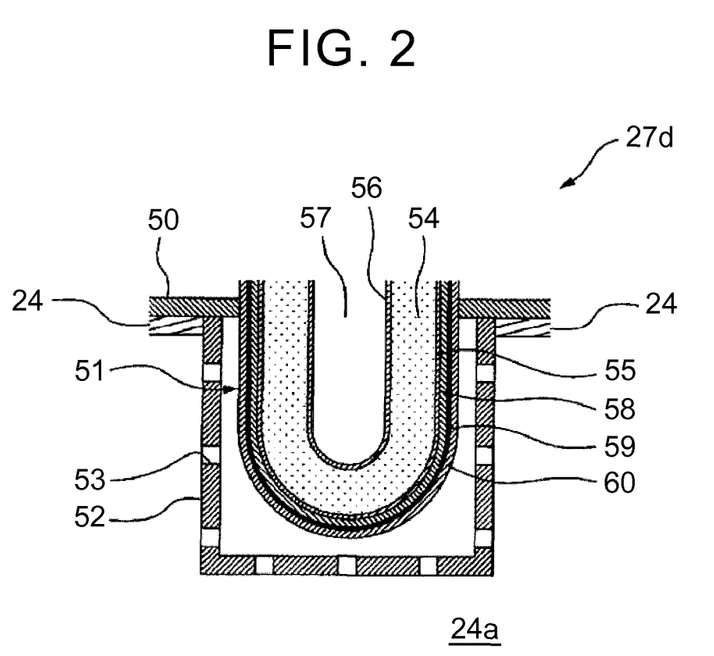
FIG. 2 is a partially enlarged cross-sectional view of a sensor for detecting oxygen concentration or an air-fuel ratio.

FIG. 2 is a partially enlarged cross-sectional view of the downstream side sensor 27d. The upstream side sensor 27u is similar in configuration to the downstream side sensor 27d. Regarding the upstream side sensor, a sensor that is different in configuration from the downstream side sensor 27d can constitute 27u.

Referring to FIG. 2, 50 represents a housing, 51 represents a sensor element that is held by the housing 50, and 52 represents a cover that has an opening 53. The sensor element 51 is provided with a cup-shaped solid electrolyte body 54, an exhaust gas side electrode 55 that is disposed on an outer surface of the solid electrolyte body 54, and a reference gas side electrode 56 that is disposed on an inner surface of the solid electrolyte body 54. The sensor element 51 and the cover 52 are arranged in an internal space 24a of the exhaust pipe 24. Accordingly, exhaust gas in the exhaust pipe 24 is introduced around the sensor element 51 via the opening 53 of the cover 52 and the exhaust gas side electrode 55 is in contact with the exhaust gas. A reference gas chamber 57 where reference gas is introduced is formed in an internal space of the solid electrolyte body 54. Accordingly, the reference gas side electrode 56 is in contact with the reference gas. In the example that is illustrated in FIG. 2, the reference gas is formed from the atmosphere. Accordingly, the reference gas side electrode 56 will also be referred to as an atmosphere side electrode. In the example that is illustrated in FIG. 2, a solid electrolyte such as zirconia forms the solid electrolyte body 54. A precious metal such as platinum forms the electrodes 55, 56.

The exhaust gas side electrode 55 is covered by a coating layer 58. The coating layer 58 is covered by a catalyst layer 59. The catalyst layer 59 is covered by a trap layer 60. The coating layer 58 protects the exhaust gas side electrode 55 and is formed of a porous ceramic such as a spinel. The catalyst layer 59 removes hydrogen in exhaust gas and is formed of a precious metal such as platinum supported on a porous ceramic such as alumina. The trap layer 60 captures a foreign matter in exhaust gas such as a deposit and is formed of a porous ceramic such as alumina.

Figure 3:
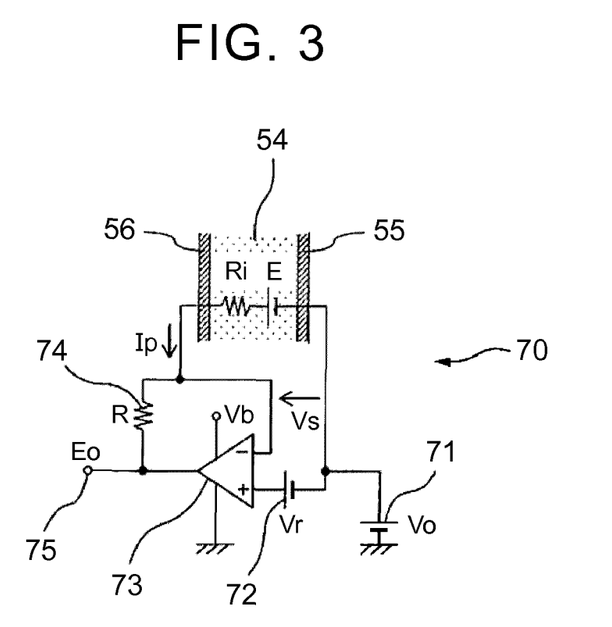
FIG. 3 is a schematic view of an electric circuit of the sensor for detecting oxygen concentration or an air-fuel ratio.

As illustrated in FIG. 3, the downstream side sensor 27d is also provided with an electric circuit 70 that applies a voltage between the electrodes 55, 56. Referring to FIG. 3, the electric circuit 70 is provided with an offset electric power supply 71 that applies an offset voltage Vo, a reference electric power supply 72 that applies a reference voltage Vr, an operational amplifier 73 to which an electric power supply voltage Vb is applied, an electric resistor 74 that applies an electric resistance R, and an output terminal 75. One side of the offset electric power supply 71 is connected to the atmosphere side electrode 56, which is a positive electrode, and the other side of the offset electric power supply 71 is connected to the reference electric power supply 72. The reference electric power supply 72 is connected to a +terminal of the operational amplifier 73. One side of the exhaust gas side electrode 55, which is a negative electrode, is connected to one terminal of the operational amplifier 73 and the other side of the exhaust gas side electrode 55 is connected to the output terminal 75 via the electric resistor 74. The output terminal 75 is input to the electronic control unit 30 (FIG. 1). The electronic control unit 30 detects an output voltage Eo, which is a potential at the output terminal 75.

The electric circuit 70 applies a voltage between the electrodes 55, 56 so that the voltage Vs between the electrodes 55, 56 is maintained at the reference voltage Vr. In this case, a current Ip flows between the electrodes 55, 56. In this case, the output voltage Eo is represented by the following Equation (1).

$$Eo = Vr + Vo + Ip \cdot R \quad (1)$$

The Equation (1) can be rewritten as the following Equation (2).

$$Ip = (Eo - Vr - Vo)/R \quad (2)$$

In the embodiment that is illustrated in FIG. 3, the output voltage Eo is detected and the output current Ip is obtained by using the Equation (2). In another embodiment, the output current Ip is directly detected. In FIG. 3, E and Ri represent an electromotive force and an internal resistance of the solid electrolyte body 54, respectively (Vs=E+Ip·Ri).

In addition, the downstream side sensor 27d is provided with a circuit that detects an impedance of the sensor element 51. The impedance of the sensor element 51 represents the temperature of the sensor element 51 or the downstream side sensor 27d.

As described above, the exhaust gas is in contact with the exhaust gas side electrode 55. Accordingly, HC and CO in the exhaust gas react with oxygen in the exhaust gas side electrode 55. As a result, the current Ip flows between the electrodes 55, 56.

Figure 4:
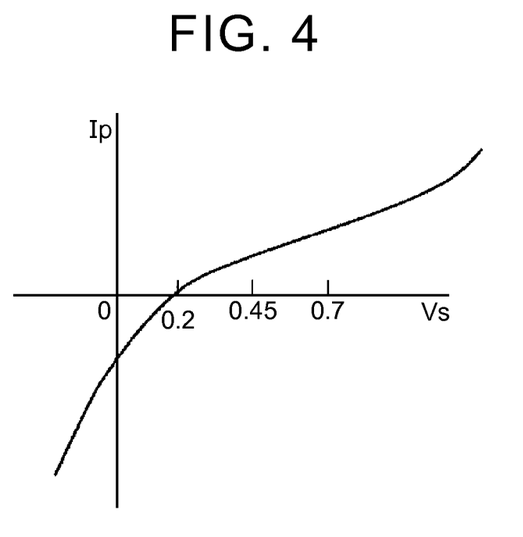
FIG. 4 is a graph illustrating a relationship between an output current and an inter-electrode voltage of a sensor for detecting oxygen concentration or an air-fuel ratio according to an embodiment of the invention.

FIG. 4 illustrates a relationship between the inter-electrode voltage Vs and the output current Ip of the downstream side sensor 27d at a time when an air-fuel ratio is maintained at a theoretical air-fuel ratio. As seen in FIG. 4, the output current Ip continues to increase as the inter-electrode voltage Vs is increased.

Figure 5:
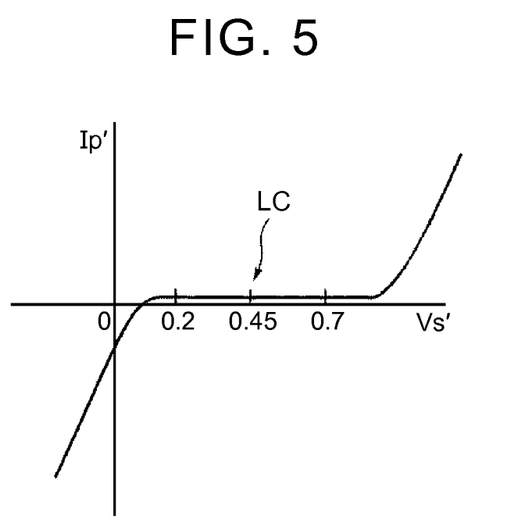
FIG. 5 is a graph illustrating a relationship between an output current and an inter-electrode voltage of a linear characteristic air-fuel ratio sensor according to the related art.

A linear characteristic air-fuel ratio sensor provided with a solid electrolyte body, an exhaust gas side electrode that is disposed on one side of the solid electrolyte body and is in contact with exhaust gas, a reference gas side electrode that is disposed on the other side of the solid electrolyte body and is in contact with reference gas, an electric circuit that applies a voltage between the electrodes, and a diffusion rate controlling layer that covers the exhaust gas side electrode is known. FIG. 5 illustrates a relationship between an output current Ip' and an inter-electrode voltage Vs' of the linear characteristic air-fuel ratio sensor at a time when an air-fuel ratio is maintained at a theoretical air-fuel ratio. As illustrated in FIG. 5, the output current Ip' increases as the inter-electrode voltage Vs' increases when the inter-electrode voltage Vs' is low. If the inter-electrode voltage Vs' further increases, the output current Ip' becomes substantially constant. If the inter-electrode voltage Vs' further increases, the output current Ip' increases as the inter-electrode voltage Vs' increases. The voltage region in FIG. 5 where the output current Ip' becomes substantially constant will be referred to as a limiting current region LC. The output current Ip' has the limiting current region LC as described above because the rate of the diffusion of the exhaust gas to the exhaust gas side electrode is controlled by the diffusion rate controlling layer. In a case where the output current Ip' has the limiting current region LC, the responsiveness of the air-fuel ratio sensor decreases and the output current Ip' may be hysteretic.

In contrast, the output current Ip of the downstream side sensor 27d according to the embodiment of the invention has no limiting current region as illustrated in FIG. 4. This is because the downstream side sensor 27d according to the embodiment of the invention is provided with no diffusion rate controlling layer. As a result, the responsiveness of the downstream side sensor 27d increases. In addition, the reference voltage Vr is applied between the electrodes 55, 56 as described above, and thus a reaction in the exhaust gas side electrode 55 is promoted. As a result, the output current Ip is not hysteretic. Accordingly, the air-fuel ratio can be accurately detected.

The coating layer 58 of the downstream side sensor 27d according to the embodiment of the invention differs in configuration from the diffusion rate controlling layer of the linear characteristic air-fuel ratio sensor in that the output current Ip is formed to have no limiting current region. Specifically, for example, the coating layer 58 has a greater porosity than the diffusion rate controlling layer of the linear characteristic air-fuel ratio sensor.

In the invention, it is determined that the output current has a limiting current region in the event of (Ip(0.7 volt)–Ip(0.45 volt))/Ip(0.45 volt)<0.05 and |Ip(0.2 volt)–Ip(0.45 volt)|/Ip(0.45 volt)<0.05 when the output current Ip at the inter-electrode voltage Vs is represented by Ip(Vs). In contrast, it is determined that the output current has no limiting current region in the event of (Ip(0.7 volt)–Ip(0.45 volt))/Ip(0.45 volt)≥0.05 or |Ip(0.2 volt)–Ip(0.45 volt)|/Ip(0.45 volt)≥0.05.

Figure 6:
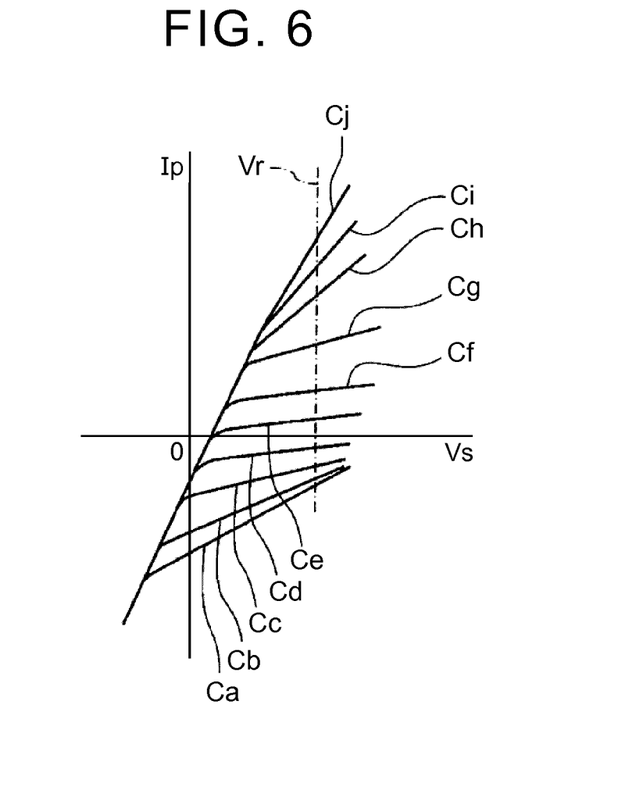
FIG. 6 is a graph illustrating the relationship between the output current and the inter-electrode voltage of the sensor for detecting oxygen concentration or an air-fuel ratio according to the embodiment of the invention.

FIG. 6 illustrates the relationship between the output current Ip and the inter-electrode voltage Vs of the downstream side sensor 27d according to the embodiment of the invention at various air-fuel ratios. In FIG. 6, curves Ca, Cb, Cc, Cd, Ce, Cf, Cg, Ch, Ci show the output current Ip in a case where the air-fuel ratio is maintained at 12, 13, 14, theoretical air-fuel ratio (14.6), 15, 18, 25, and 40 each. A curve Cj shows the output current Ip in a case where the atmosphere is in contact with the exhaust gas side electrode 55. As seen in FIG. 6, the output current Ip increases as the air-fuel ratio increases.

Figure 7:
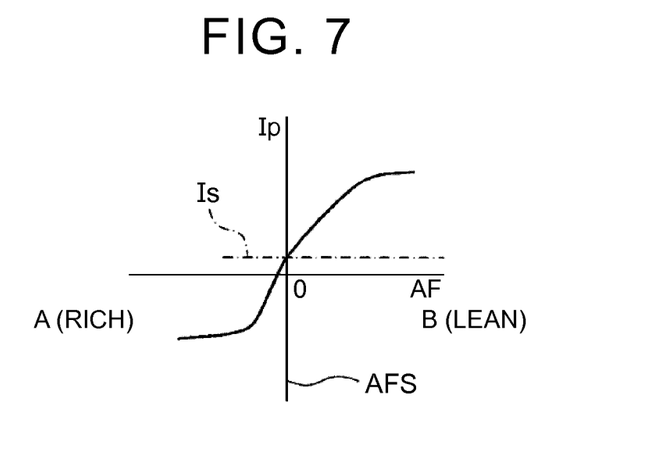
FIG. 7 is a graph illustrating a relationship between the output current of the sensor for detecting oxygen concentration or an air-fuel ratio according to the embodiment of the invention and an air-fuel ratio.

FIG. 7 illustrates a relationship between an air-fuel ratio AF and the output current Ip of the downstream side sensor 27d according to the embodiment of the invention in a case where the inter-electrode voltage Vs is maintained at the reference voltage Vr. As seen in FIG. 7, the output current Ip increases as the air-fuel ratio AF increases. In addition, the output current Ip becomes equal to a reference current Is (>0) when the air-fuel ratio AF is equal to a reference air-fuel ratio. In the example that is illustrated in FIG. 7, the reference air-fuel ratio is equal to the theoretical air-fuel ratio.

As described above, the oxygen concentration in the exhaust gas or the air-fuel ratio can be detected from the output current Ip of the downstream side sensor 27d. In the embodiment of the invention, the air-fuel ratio AF is determined to be lower than a theoretical air-fuel ratio AFS, that is, to be richer than the theoretical air-fuel ratio AFS when the output current Ip is less than the reference current Is and the air-fuel ratio AF is determined to be higher than the theoretical air-fuel ratio AFS, that is, to be leaner than the theoretical air-fuel ratio AFS when the output current Ip is greater than the reference current Is.

Then, the air-fuel ratio is controlled based on the determination result. For example, the air-fuel ratio AF is controlled to be increased when the air-fuel ratio AF is determined to be lower than the theoretical air-fuel ratio AFS based on the output current Ip of the downstream side sensor 27d and the air-fuel ratio AF is controlled to be decreased when the air-fuel ratio AF is determined to be higher than the theoretical air-fuel ratio AFS based on the output current Ip of the downstream side sensor 27d. In this example, the air-fuel ratio AF is controlled with the theoretical air-fuel ratio AFS, that is, the reference air-fuel ratio being a target value. The air-fuel ratio AF is controlled by, for example, controlling a fuel injection amount or an intake air amount.

The reference voltage Vr is set so that a change in the output current Ip with respect to the air-fuel ratio AF near the reference air-fuel ratio increases. In this case, it can be more accurately detected whether the air-fuel ratio AF is lower or higher than the reference air-fuel ratio.

Figure 8:
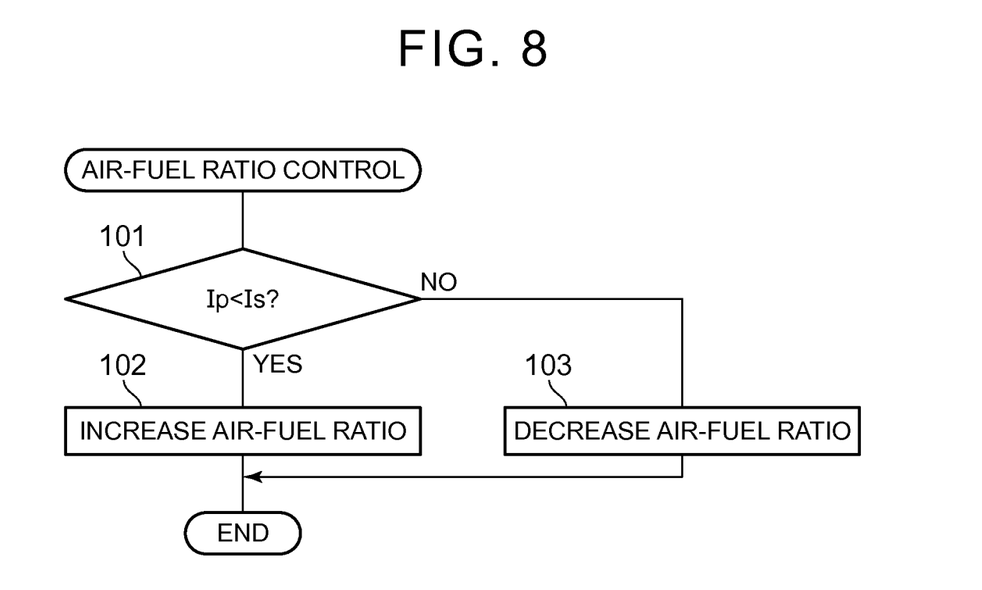
FIG. 8 is a flowchart for executing an air-fuel ratio control routine.

FIG. 8 illustrates a routine for executing the air-fuel ratio control described above. Referring to FIG. 8, it is determined in Step 101 whether or not the output current Ip of the downstream side sensor 27d is less than the reference current Is. The routine proceeds to Step 102 when Ip is less than Is, and the air-fuel ratio is controlled to be increased. The routine proceeds to Step 103 when Ip is equal to or greater than Is, and the air-fuel ratio is controlled to be decreased.

Next, another embodiment of the invention will be described. In the following description, differences from the embodiment that is illustrated in FIGS. 1 to 8 will be described.

Figure 9A:
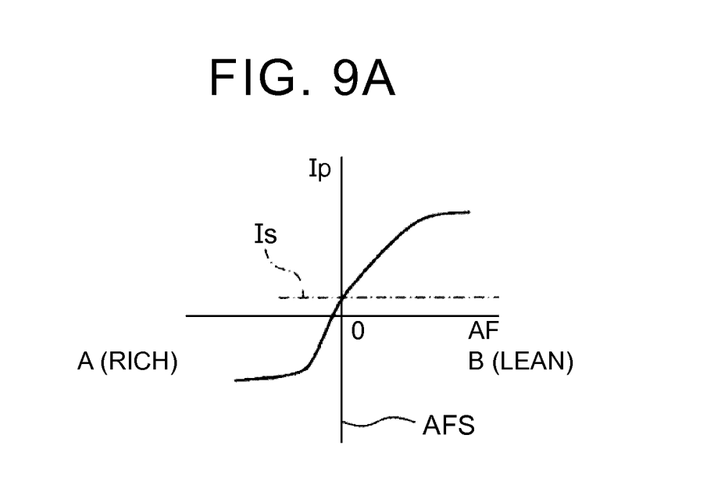
FIG. 9A is a graph illustrating a relationship between an output current of a sensor for detecting oxygen concentration or an air-fuel ratio and an air-fuel ratio.
Figure 9B:
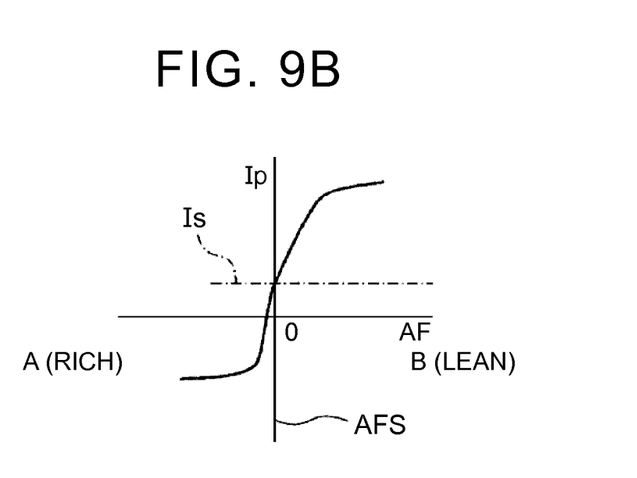
FIG. 9B is a graph illustrating a relationship between an output current of a sensor for detecting oxygen concentration or an air-fuel ratio and an air-fuel ratio.

FIG. 9A illustrates the output current Ip at a time when the temperature of the downstream side sensor 27d is relatively low and FIG. 9B illustrates the output current Ip at a time when the temperature of the downstream side sensor 27d is relatively high. As seen in FIGS. 9A and 9B, the output current Ip increases as the temperature of the downstream side sensor 27d increases. Accordingly, the detection may be erroneous if the air-fuel ratio is detected based on the constant reference current Is.

Figure 10:
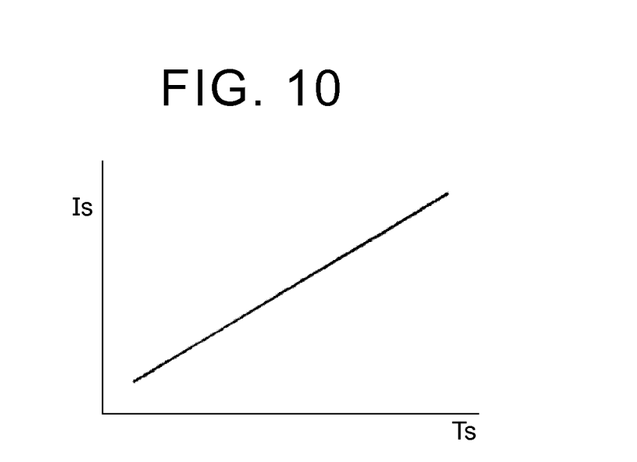
FIG. 10 is a graph illustrating a reference current Is.

In this another embodiment of the invention, the reference current Is is set based on a temperature Ts of the downstream side sensor 27d. Specifically, the reference current Is is set to increase as the temperature Ts of the downstream side sensor 27d increases as illustrated in FIG. 10. As a result, the air-fuel ratio can be accurately detected regardless of the temperature Ts of the downstream side sensor 27d, and thus the air-fuel ratio can be accurately controlled. The reference current Is is stored in the ROM 32 in advance in the form of the map that is illustrated in FIG. 10.

Figure 11:
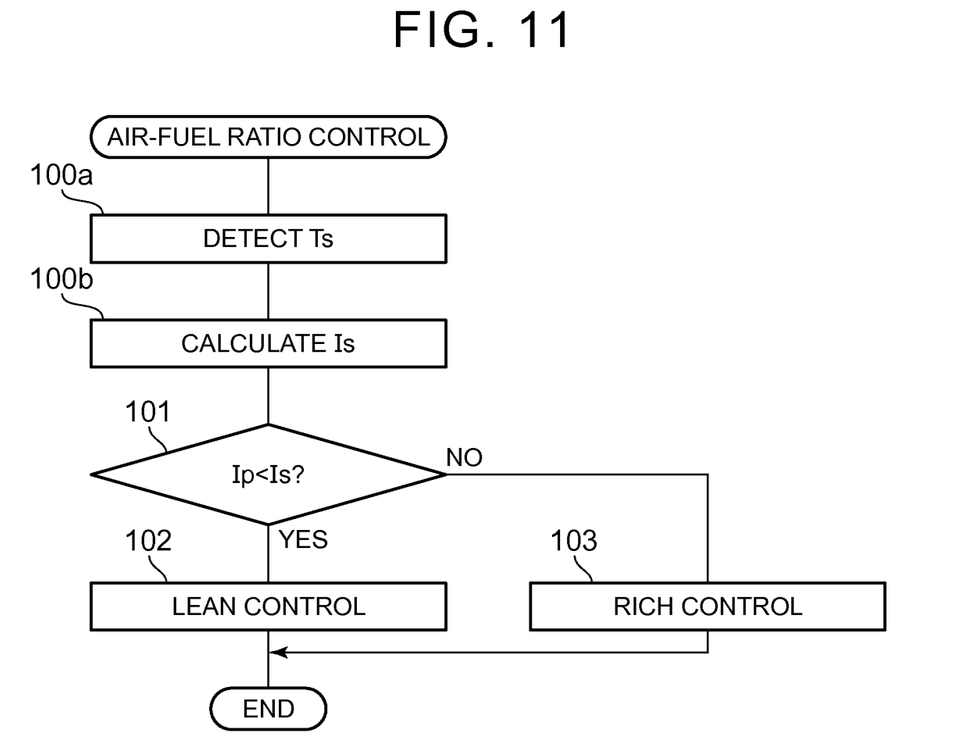
FIG. 11 is a flowchart for executing an air-fuel ratio control routine according to another embodiment of the invention.

FIG. 11 illustrates a routine for executing air-fuel ratio control according to this another embodiment of the invention. Referring to FIG. 11, the temperature Ts of the downstream side sensor 27d is detected in Step 100a. Then, the reference current Is is calculated from the map of FIG. 10 in Step 100b. Then, it is determined in Step 101 whether or not the output current Ip of the downstream side sensor 27d is less than the reference current Is. The routine proceeds to Step 102 when Ip is less than Is, and the air-fuel ratio is controlled to be increased. The routine proceeds to Step 103 when Ip is equal to or greater than Is, and the air-fuel ratio is controlled to be decreased.

Next, yet another embodiment of the invention will be described. In the following description, differences from the embodiment that is illustrated in FIGS. 1 to 8 will be described.

In the embodiment described above, the reference voltage Vr is set so that the reference current Is has a positive value. In contrast, the reference voltage Vr is set so that the reference current Is becomes zero in this yet another embodiment of the invention. In this case, a detection error can be reduced.

Figure 12A:
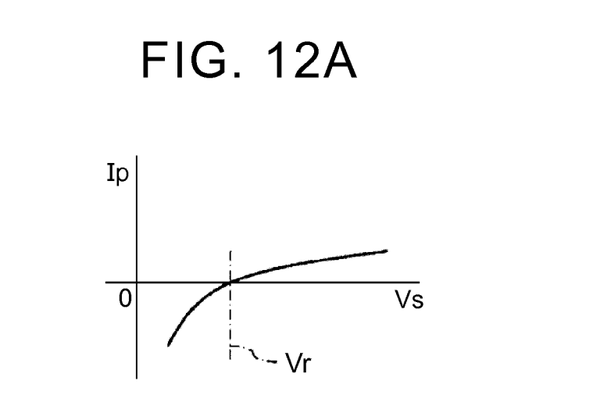
FIG. 12A is a graph illustrating a relationship between an output current and an inter-electrode voltage of a sensor for detecting oxygen concentration or an air-fuel ratio.
Figure 12B:
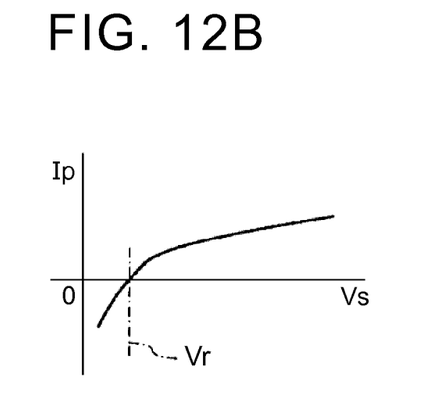
FIG. 12B is a graph illustrating a relationship between an output current and an inter-electrode voltage of a sensor for detecting oxygen concentration or an air-fuel ratio.

FIG. 12A illustrates a relationship between the output current Ip and the inter-electrode voltage Vs at a time when the temperature Ts of the downstream side sensor 27d is relatively low and FIG. 12B illustrates a relationship between the output current Ip and the inter-electrode voltage Vs at a time when the temperature of the downstream side sensor 27d is relatively high. As seen in FIGS. 12A and 12B, the reference voltage Vr at which the output current Ip becomes zero decreases when the temperature of the downstream side sensor 27d increases. Accordingly, the detection may be erroneous if the air-fuel ratio is detected based on the output current Ip detected while applying the constant reference voltage Vr.

Figure 13:
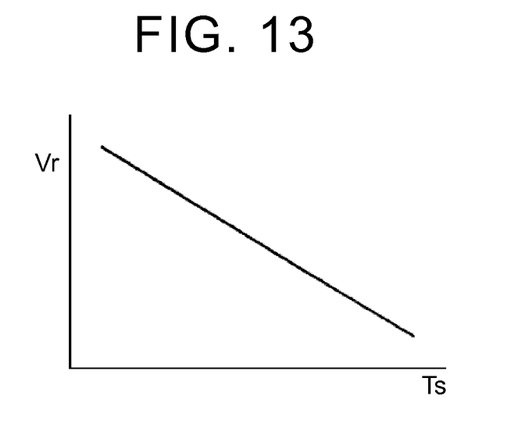
FIG. 13 is a graph illustrating a reference voltage Vr.

In this yet another embodiment of the invention, the reference voltage Vr is set based on the temperature Ts of the downstream side sensor 27d. Specifically, the reference voltage Vr is set to be decreased as the temperature Ts of the downstream side sensor 27d increases as illustrated in FIG. 13. As a result, the air-fuel ratio can be accurately detected regardless of the temperature Ts of the downstream side sensor 27d, and thus the air-fuel ratio can be accurately controlled. The reference voltage Vr is stored in the ROM 32 in advance in the form of the map that is illustrated in FIG. 13.

Figure 14:
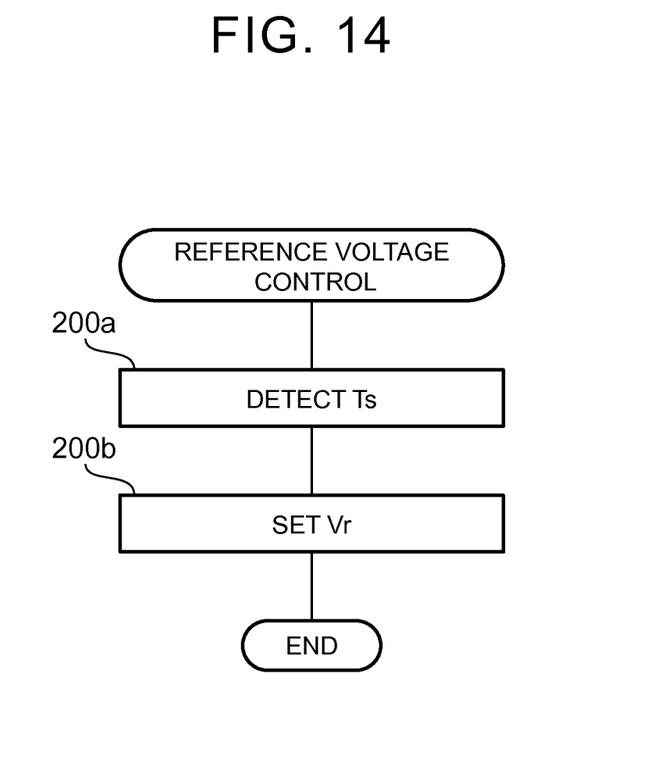
FIG. 14 is a flowchart for executing a reference voltage control routine.

FIG. 14 illustrates a routine for executing reference voltage control according to this yet another embodiment of the invention. Referring to FIG. 14, the temperature Ts of the downstream side sensor 27d is detected in Step 200a. Then, the reference voltage Vr is calculated from the map of FIG. 13 in Step 200b. In the downstream side sensor 27d, the inter-electrode voltage Vs is maintained at the reference voltage Vr that is calculated in this manner.

REFERENCE SIGNS LIST

1 Engine main body
22 Exhaust manifold
24, 26 Exhaust pipe
23a, 25a Three-way catalyst
27u, 27d Sensor for detecting oxygen concentration or air-fuel ratio
54 Solid electrolyte body
55 Exhaust gas side electrode
56 Reference gas side electrode
70 Electric circuit

What is claimed is:

1. A control device for an internal combustion engine, the control device comprising:
a sensor configured to detect an oxygen concentration in an exhaust gas or an air-fuel ratio, the sensor being arranged in an exhaust passage of the internal combustion engine, the sensor including a solid electrolyte body, an exhaust gas side electrode, a reference gas side electrode, and an electric circuit, the exhaust gas side electrode being disposed on one side of the solid electrolyte body and being in contact with the exhaust gas, the reference gas side electrode being disposed on the other side of the solid electrolyte body and being in contact with reference gas, the electric circuit applying a reference voltage between the exhaust gas side electrode and the reference gas side electrode, and the sensor is provided with no diffusion rate controlling layer and a coating layer having a porosity such that said sensor has a characteristic in which an output current continues to increase without having a limiting current region when the voltage applied between the exhaust gas side electrode and the reference gas side electrode is increased while the air-fuel ratio is constant; and an electronic control unit configured to control the air-fuel ratio based on the output current of the sensor, wherein the sensor has a characteristic in which the output current increases as the air-fuel ratio increases, wherein the electronic control unit is configured to determine that the air-fuel ratio is lower than a reference air-fuel ratio when the output current is less than a reference current corresponding to the reference air-fuel ratio, wherein the electronic control unit is configured to determine that the air-fuel ratio is higher than the reference air-fuel ratio when the output current is greater than the reference current, wherein the reference current corresponds to the reference air-fuel ratio, wherein the electronic control unit is configured to control the air-fuel ratio based on the determination result, wherein the reference air-fuel ratio is equal to a theoretical air-fuel ratio, and wherein the reference voltage is set such that when applying the reference voltage between the exhaust gas side electrode and the reference gas side electrode the output current of the sensor is equal to the reference current and is equal to zero.

2. The control device according to claim 1, wherein the electronic control unit is configured to set the reference current based on the temperature of the sensor.

3. The control device according to claim 2, wherein the electronic control unit is configured to increase the reference current as the temperature of the sensor increases.

4. The control device according to claim 1, wherein the reference voltage is set such that the reference current has a positive value.

5. The control device according to claim 1, wherein the reference gas comprises an atmospheric gas.

* * * * *